United States Patent
Tang et al.

(10) Patent No.: US 8,101,102 B2
(45) Date of Patent: Jan. 24, 2012

(54) METHOD FOR IMPROVING THE RESISTANCE OF FUMIGANT SORPTION IN AN EXPANDABLE POLYMER PRODUCE CONTAINER AND A RELATED CONTAINER

(75) Inventors: Jiansheng Tang, Mars, PA (US); Michael T. Williams, Beaver Falls, PA (US); David A. Cowan, Cranberry Township, PA (US)

(73) Assignee: NOVA Chemicals Inc., Moon Township, PA (US)

( * ) Notice: Subject to any disclaimer, the term of this patent is extended or adjusted under 35 U.S.C. 154(b) by 882 days.

(21) Appl. No.: 11/633,203

(22) Filed: Dec. 4, 2006

(65) Prior Publication Data

US 2007/0148386 A1  Jun. 28, 2007

Related U.S. Application Data

(60) Provisional application No. 60/753,307, filed on Dec. 22, 2005.

(51) Int. Cl.
*B32B 37/00* (2006.01)
*A23B 4/16* (2006.01)
*B29D 22/00* (2006.01)
*C08J 9/00* (2006.01)

(52) U.S. Cl. .......... 264/45.5; 264/25; 521/50; 428/35.7; 426/316

(58) Field of Classification Search .............. 264/45.5, 264/25; 428/36.5, 35.7; 521/50; 426/316
See application file for complete search history.

(56) References Cited

U.S. PATENT DOCUMENTS

| | | | |
|---|---|---|---|
| 2,656,334 A | 10/1953 | D'Alelio | |
| 2,983,692 A | 5/1961 | D'Alelio | |
| 3,023,175 A | 2/1962 | Rodman, Jr. | |
| 3,817,965 A | 6/1974 | Mace et al. | |
| 3,968,879 A | 7/1976 | Lucas, Sr. et al. | |
| 4,104,440 A | 8/1978 | Collins | |
| 4,781,983 A | 11/1988 | Stickley | |
| 5,016,777 A | 5/1991 | Marvin | |
| 5,318,789 A * | 6/1994 | Nakagawa et al. | 426/316 |
| 5,690,272 A | 11/1997 | England | |
| 6,127,439 A | 10/2000 | Berghmans et al. | |
| 6,160,027 A | 12/2000 | Crevecoeur et al. | |
| 6,242,540 B1 | 6/2001 | Crevecoeur et al. | |
| 6,623,674 B1 * | 9/2003 | Gehlsen et al. | 264/45.5 |
| 2002/0117769 A1 | 8/2002 | Arch et al. | |
| 2004/0121101 A1* | 6/2004 | Tang et al. | 428/36.5 |
| 2005/0153088 A1 | 7/2005 | Russell et al. | |

FOREIGN PATENT DOCUMENTS

EP   0 488 040 A2   11/1991
GB   1 409 285     10/1975

* cited by examiner

*Primary Examiner* — Christina Johnson
*Assistant Examiner* — Michael Piery
(74) *Attorney, Agent, or Firm* — Gary F. Matz

(57) ABSTRACT

A method for improving the resistance of fumigant sorption in a produce container made of expandable polystyrene particles in a fumigation process, and related produce container. Expandable polystyrene particles having a density ranging from 40.0 to 32.0 pounds per cubic foot and a blowing agent amount ranging from 2.5 to 7.5 weight percent are pre-expanded to form pre-expanded particles having a core bulk density ranging from 12.5 to 2.0 pounds per cubic foot, and a skin density ranging between 40.0 and 32.0 pounds per cubic foot and a thickness ranging from 0.1 to 2 microns. These pre-expanded particles are injected into a mold to form a produce container having a wall thickness ranging from 0.25 to 2.0 inches.

8 Claims, 1 Drawing Sheet

METHOD FOR IMPROVING THE RESISTANCE OF FUMIGANT SORPTION IN AN EXPANDABLE POLYMER PRODUCE CONTAINER AND A RELATED CONTAINER

CROSS REFERENCE TO RELATED PATENT APPLICATION

The present non-provisional patent application is entitled to and claims, under 35 U.S.C. §119(e), the benefit of U.S. Provisional Patent Application No. 60/753,307, filed Dec. 22, 2005, which is hereby incorporated herein in its entirety by reference.

BACKGROUND OF THE INVENTION

1. Field of the Invention

The present invention relates to a produce container made of expandable polymer particles, e.g. expandable polystyrene particles (EPS), and to a method for improving the resistance of fumigant, e.g. methyl bromide, sorption in a produce container made of expandable polymer particles in a fumigation process.

2. Background Art

Fumigants are used to eradicate pests from containers for the international shipment of produce, e.g. grapes, tomatoes, etc. In general, the fumigation process is necessary when produce, e.g. fruits and/or vegetables are either imported or exported in order to control the infestations of pests, e.g. Mediterranean fruit fly. A commonly used fumigant is methyl bromide, which is highly toxic.

The types of containers most commonly used for shipping produce are made of wood, paperboard, or plastic materials, e.g. expandable polystyrene particles. Wooden containers need to be inexpensive and yet sturdy and recently the cost of wood has become prohibitive. Cardboard or paperboard containers tend to collapse when a number of filled containers are stacked on top of each other. A container made of expandable polystyrene particles provides the sturdiness needed to support the number of filled containers when stacked on top of each other and is relatively inexpensive compared to wooden containers. Examples of containers made of expandable polystyrene particles in a molding process are disclosed in U.S. Pat. No. 5,016,777 issued to Morley Marvin on May 21, 1991 and in U.S. Pat. No. 5,690,272 issued to James England on Nov. 25, 1997. The latter patent discloses a container that is hand assembled and is suitable for shipping produce.

However, due to the nature of foamed polymer, e.g. polystyrene, in that it contains open cells or voids, produce containers made of expandable polymer particles have a relatively high fumigant absorption rate compared to produce containers made of wood or paperboard. Additionally, the fumigant tends to remain desorbed in the walls of the container of from expandable polymer particles for a long period of time after the fumigation process.

When produce is imported into or exported from a country, the general procedure is to stack two or more rows of produce containers containing the vegetables or fruits onto a pallet, and then transport the pallet into a fumigation chamber. The fumigant, which typically is methyl bromide, is delivered into the chamber for two hours in order to kill any infestation that may be present, and then the delivery of the fumigant is discontinued for the next two hours so that the methyl bromide can dissipate before the chamber can be safely opened to remove the pallet and containers.

The United States Department of Agriculture (USDA) requires that the fumigation process meet the following criteria: 1) The methyl bromide concentration in the fumigation chamber during the fumigation process should not be lower than the minimum concentration required by USDA schedule T101-I-2-1, e.g. 48 ounces/1000 feet$^3$ for the first half hour and 38 ounces/1000 feet$^3$ for 2.0 hours, at 40-49° F. 2) The residual methyl bromide concentration should not be more than 5 ppm after degassing, i.e. removing the methyl bromide from the chamber.

Studies have shown that the current produce containers made of expandable polystyrene particles cannot maintain the mandated minimum methyl bromide concentrations during the fumigation process when the initial concentration required by USDA (64 ounces/1000 feet$^3$) is applied in that these containers absorb a great amount of methyl bromide. Data also show that these containers have a high residual concentration (higher than the threshold limit value (TLV) of 5 ppm) after a typical aeration process following the fumigation process.

Therefore, the produce market requires improved expandable polymer, e.g. polystyrene, containers that absorb and retain and retain less fumigant during the fumigation process.

There is a further need to provide a testing procedure for detecting the sorption of a fumigant in a produce container, especially made of expandable polymer particles.

Additionally, there is a need to provide a method for improving the resistance of fumigant, e.g. methyl bromide, sorption in a produce container made of expandable polystyrene (EPS) particles.

SUMMARY OF THE INVENTION

The invention has met the above needs. The present invention provides a method for improving the resistance of fumigant sorption in a produce container made of expandable polystyrene particles in a fumigation process. This method involves the steps comprising: pre-expanding the expandable polystyrene particles with a density of about 40.0 to about 32.0 pounds per cubic foot to produce pre-expanded articles with a relatively low density core, i.e. a bulk density ranging from about 12.5 pounds per cubic foot to about 2.0 pounds per cubic foot and a relatively higher density skin, i.e. ranging from about 40.0 to about 32.0 pounds per cubic foot and wherein the skin has a wall thickness of from about 0.1 micron to about 2.0 microns; and injecting these pre-expanded particles into a mold to produce a container having a wall thickness ranging from about 0.25 inch to about 2.0 inches.

A further embodiment of the present invention provides a produce container made of expandable polystyrene particles in a fumigation process, the steps comprising: subjecting expandable polystyrene particles having a density of about 40.0 to about 32.0 pounds per cubic foot to an expansion process to produce expanded polystyrene particles with a relatively low density core, i.e. a bulk density ranging from about 12.5 pounds per cubic foot to about 2.0 pounds per cubic foot and with a relatively higher density skin, i.e. ranging from about 40.0 to about 32.0 pounds per cubic foot and a wall thickness ranging from about 0.1 micron to about 2.0 microns, to form pre-expanded particles; and injecting these pre-expanded particles into a mold to produce a container with a wall thickness ranging from about 0.25 inch to about 2.0 inches.

A further embodiment of the present invention provides a method of improving the resistance of fumigant sorption in a produce container made of expandable polystyrene particles in a fumigation process, the steps comprising producing expandable particles having a density of about 40.0 to about 32.0 pounds per cubic feet to an expansion process;

expanding the expandable particles to form pre-expanded particles having a relatively low density core and a relatively higher density skin, wherein the core has a bulk density ranging from about 2 to about 12.5 pounds per cubic foot (PCF) and the skin has a density ranging from about 40.0 to about 32.0 pounds per cubic foot (PCF) and a thickness ranging from about 0.1 micron to about 2.0 microns; and using the pre-expanded particles to form a produce container.

A further embodiment of the invention pertains to a produce container having a wall thickness ranging from about 0.25 inch to about 2.0 inches.

These and other aspects of the invention will be more fully appreciated and understood from the following description and the appended claims.

DETAILED DESCRIPTION OF THE INVENTION

Figure 1:
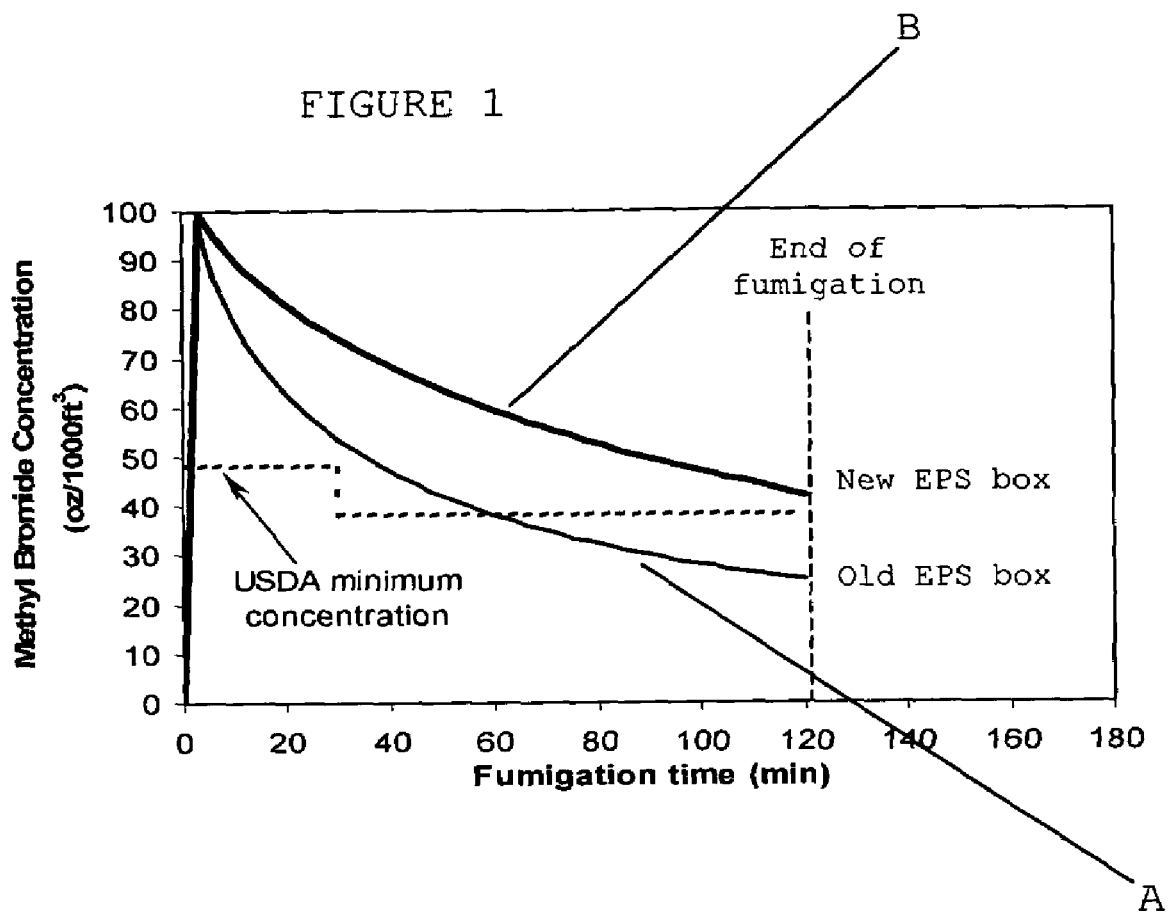
FIG. 1 is a graph showing the methyl bromide concentrations (ounces/1000 feet$^3$) versus fumigation time (minutes) for the USDA minimum requirement for the present or current (old) EPS containers indicated at "A" and for the inventive (new) EPS containers indicated at "B".

The inventors have found solutions to providing produce containers, made of expandable polystyrene (EPS) particles, with improved resistance to methyl bromide in a fumigation process from a physical approach. The findings were:

1. Methyl bromide sorption in produce containers is dependent on the volume of the container material, i.e. less EPS foam volume results in less methyl bromide sorption.

2. Thin-wall produce containers, which use less EPS foam material is favorable in the fumigation process.

3. Methyl bromide is mainly absorbed by the cells of the EPS foam material, and therefore, a larger cell size or particle size would decrease both the volume of the EPS foam material and also would decrease the methyl bromide absorption.

4. A relatively thick skin on the EPS particles tends to retard the penetration of methyl bromide into the produce container.

The produce container of the invention is molded from expandable polymer particles, which are made from any suitable homopolymers or copolymers. Particularly suitable for use are homopolymers derived from vinyl aromatic monomers including styrene, isopropylstyrene, alpha-methylstyrene, nuclear methylstyrenes, chlorostyrene, tert-butylstyrene, and the like, as well as copolymers prepared by the copolymerization of at least one vinyl aromatic monomer with monomers such as divinylbenzene, butadiene, alkyl methacrylates, alkyl acrylates, acrylonitrile, and maleic anhydride, wherein the vinyl aromatic monomer is present in at least 50% by weight of the copolymer.

In most embodiments, the styrenic polymers may be polystyrene. However, other suitable polymers may be used, such as polyolefins (e.g. polyethylene, polypropylene), and polycarbonates, polyphenylene oxides, and mixtures thereof. Preferably, in the embodiments, the expandable thermoplastic particles are expandable polystyrene (EPS) particles.

The particles may be in the form of beads, granules, or other particles convenient for expansion and molding operations. Particles polymerized in an aqueous suspension process are essentially spherical and are preferred for molding the foam containers of the invention.

The expandable polystyrene particles are impregnated with a suitable blowing agent using any conventional method. For example, the impregnation can be achieved by adding the blowing agent to the aqueous suspension during the polymerization of the polymer, or alternatively by re-suspending the polymer particles in an aqueous medium and then incorporating the blowing agent as taught in U.S. Pat. No. 2,983,692 to D. Alelio.

Any gaseous material or material which will produce gases on heating can be used as the blowing agent. Conventional blowing agents include aliphatic hydrocarbons containing 4 to 6 carbon atoms in the molecule, such as butanes, pentanes, hexanes, and the halogenated hydrocarbons, e.g. CFC's and HCFC's, which boil at a temperature below the softening point of the chosen polymer. Mixtures of the aliphatic hydrocarbons blowing agents can also be used.

Alternatively, water can be blended with these aliphatic hydrocarbons blowing agents or water can be used as the sole blowing agent as taught in U.S. Pat. Nos. 6,127,439; 6,160,027; and 6,242,540 assigned to NOVA Chemicals (International) S.A. In the aforesaid patents, water-retaining agents are used. The weight percentage of water for use as the blowing agent can range from 1 to 20%. The teachings of U.S. Pat. Nos. 6,127,439, 6,160,027 and 6,242,540 in their entirety are incorporated herein by reference.

The manufacture of molded foam containers, e.g. produce containers for shipping produce, e.g. fruits e.g. grapes and vegetables, e.g. tomatoes, from thermoplastic particles, i.e. expandable polystyrene (EPS) particles, is well known.

Typically, the polystyrene beads or particles are impregnated with a hydrocarbon, e.g. pentane, as a blowing agent, which boils below the softening point of the polystyrene thereby causing the particles to expand when heated. The amount of blowing agent impregnated in the polymer may range from about 4.0 to about 9.0 weight percent.

The expandable polystyrene particles may be obtained by polymerization, and the blowing agent may be incorporated into the polymer before, during, or after the polymerization process. A preferred polymerization process for the production of expandable polystyrene particles is suspension polymerization.

A preferred polymerization process for the production of expandable polystyrene particles is suspension polymerization. In this process, a polymer composition is polymerized in an aqueous suspension in the presence of from 0.1 to 1.0% by weight of a free radical initiator and the blowing agent.

For the suspension polymerization many methods and initiators are known to those skilled in the art. In this respect reference is made to e.g., U.S. Pat. Nos. 2,656,334 and 3,817,965 and European Patent Application No. 488,040. The initiators disclosed in these references can also be used to make the expandable particles that in turn are used to make the pre-expanded particles of the present invention. Suitable initiators are organic peroxy compounds, such as peroxides, peroxy carbonates and peresters. Typical examples of these peroxy compounds are $C_{6-20}$ acyl peroxides, such as decanoyl peroxide, benzoyl peroxide, octanoyl peroxide, stearyl peroxide, peresters, such as t-butyl perbenzoate, t-butyl peracetate, t-butyl perisobutyrate, t-butylperoxy 2-ethylhexyl carbonate, carbonoperoxoic acid, OO-(1,1-dimethylpropyl) O-(2-ethylhexyl) ester, hydroperoxides and dihydrocarbyl peroxides, such as those containing $C_{3-10}$ hydrocarbyl moieties, including di-isopropyl benzene hydroperoxide, di-t-butyl peroxide, dicumyl peroxide or combinations thereof. Other initiators, different from peroxy compounds, are also possible, as for example $\alpha,\alpha'$-azobisisobutyronitrile.

The suspension polymerization is carried out in the presence of suspension stabilizers. Suitable suspension stabilizers are well known in the art and comprise organic stabilizers, such as poly (vinyl alcohol), gelatine, agar, polyvinyl pyrrolidine, polyacrylamide; inorganic stabilizers, such as alumina, bentonite, magnesium silicate; surfactants, such as sodium dodecyl benzene sulfonate; or phosphates, like tricalciumphosphate, disodium-hydrogen phosphate, optionally in combination with any of the stabilizing compounds mentioned earlier. The amount of stabilizer may suitably vary from 0.001 to 0.9% by weight, based on the weight of the aqueous phase.

The expandable particles may also contain an anti-static additive; a flame retardant; a colorant or dye; a filler material, such as carbon black, titanium dioxide, aluminum, and graphite, which are generally used to reduce thermal conductivity; stabilizers; and plasticizers, such as white oil or mineral oil. The particles may suitably be coated with coating compositions comprised of white oil or mineral oil, silicones, metal or glycerol carboxylates, suitable carboxylates being glycerol mono-, di- and tri-stearate, zinc stearate, calcium stearate, and magnesium stearate; and mixtures thereof. Examples of such compositions have been disclosed in GB Patent No. 1,409,285 and in Stickley U.S. Pat. No. 4,781,983.

In the invention, the formation of molded containers from impregnated polystyrene particles is generally done in two steps. First, the impregnated particles are pre-expanded to form particles having a core bulk density ranging from about 2.0 to about 12.5 pounds per cubic foot and an outer skin with a density ranging from about 40.0 to about 32.0 pounds per cubic foot and a wall thickness ranging from around 0.1 to about 2.0 microns. Second, the pre-expanded particles ("pre-puff") are heated in a closed mold to further expand the pre-expanded particles to fuse the beads together to form a foam article, e.g. produce containers, having the shape of the mold and a wall thickness ranging from about 0.25 inch to 2.0 inches.

The pre-expansion step is conventionally carried out by heating the impregnated beads via any conventional heating medium, such as steam, hot air, hot water, or radiant heat. One generally accepted method for pre-expanding impregnated thermoplastic particles is taught in U.S. Pat. No. 3,023,175 to Rodman.

In some embodiments, the expandable polystyrene particles are pre-expanded to form particles having a core and an outer skin. The core has a relatively lower density than the skin, i.e. the core has a bulk density ranging from about 2.0 to about 12.5 pounds per cubic foot, and the outer skin has a relatively higher density ranging from about 40.0 to about 32.0 pounds per cubic foot and a wall thickness ranging from about 0.1 micron to about 2.0 microns. The pre-expandable particles may contain a volatile blowing agent in an amount less than 10.0% by weight, preferably from about 2.0% by weight to about 7.5% by weight, and more preferably ranging from about 3.5% to about 6.5% by weight, based on the weight of the polymer.

As stated herein above, the expandable polystyrene particles used to make foam containers are generally prepared in an aqueous suspension polymerization process, which results in particles that can be screened to relatively precise particle sizes. Typically, the raw particle diameters for making containers are greater than 300 microns. Typically, these raw particles, which are expandable, i.e. not expanded, have a density of about 40.0 to about 32.0 pounds per cubic foot.

In an embodiment of the invention, a method of improving the resistance of fumigant sorption in a produce container made of expandable polystyrene particles in a fumigation process, involves the steps of starting with expandable particles, i.e. not expanded, pre-expanding these expandable polystyrene particles, aging these pre-expanded particles, and injecting these particles into a mold having the shape of a produce container to produce a produce container with a wall thickness ranging between about 0.25 to about 2.0 inches.

A further embodiment of the invention involves a method of improving the resistance of fumigant sorption in a produce container made of expandable polystyrene particles by increasing the particle size or volume of the expandable polystyrene particles, and therefore, decreasing the particle density, and then injecting these particles in a mold having the shape of a produce container. This is accomplished by producing the expandable particles through a suspension process as taught herein above to produce particles having a density of about 40.0 to about 32.0 pounds per cubic and a blowing agent ranging from about 2.5 to about 7.5 weight percent based on the weight of the particles, pre-expanding these particles, aging them; and injecting these particles into a mold to produce a produce container.

In some embodiments, the particle size of the expandable, i.e. non-expanded particles will range from about 0.25 mm to about 1.0 mm, and preferably, from about 0.50 mm to about 1.2 mm, and particle size of the pre-expanded particles will be greater than 3.0 microns, e.g. 300 microns.

An additional embodiment of the invention involves a method for improving the resistance of fumigant sorption in a produce container by providing expandable polystyrene particles having a relatively low density core and a skin of relatively higher density, pre-expanding these particles, and then injecting the pre-expanded particles into a mold having the shape of a produce container.

The drying process for expandable particles typically involves directing a stream of hot air at a temperature range of 50° C. to about 110° C., preferably 80° C. to about 100° C., onto the surface of the expandable polystyrene particles for about 1 minute to sixty minutes.

The present invention is further illustrated in the following examples; however, without restricting its scope.

EXAMPLES

In the examples, a prototype chamber testing method for measuring methyl bromide sorption was devised which employs a simple chamber set-up and an effective data analysis model to precisely and conveniently evaluate the fumigant sorption in molded expandable polystyrene particles.

An open testing chamber was set up and consisted of a rectangular stainless steel container with a specific volume of either 6.43 liters (0.227 cubic feet) or 141.7 litters (5.0 cubic feet). A flat stainless steel cover was placed on top of the chamber and sealed with a strip of caulking for a gas-tight fit. Methyl bromide gas was introduced into the chamber using a gas-tight syringe with an aliquot, which gas was taken from a bag made from TEDLAR® (E.I. DuPont DeNemours & Company) films or sheets of polymers of vinyl fluoride. The bag was first filled with pure gas, which, in turn, was obtained from a cylinder of standard fumigation grade methyl bromide.

The sealed testing chamber was placed in a small cubical area equipped with an air conditioner for controlling the external temperature of the produce container to a temperature of about 45° F. while the testing chamber was injected with the methyl bromide gas at a dosage rate of about 4.0 pounds per 1000 cubic feet. The gas in the chamber was sampled with a portable gas chromatograph, which was calibrated with methyl bromide.

Data was collected every 180 seconds over a four hour period. The first two-hour period is the static exposure period where the container is exposed to the methyl bromide gas at a dosage rate of about 4.0 pounds per cubic foot. The second two-hour period is referred to as the dynamic aeration period. During this time, an external pump is actuated to introduce aeration air into the chamber, which exchanges the methyl bromide gas for clean air in the chamber at a rate of 2 to 3 air volumes per minute. Data were collected during this time as well.

Example 1

Expandable polystyrene particles were prepared in a typical suspension polymerization process as discussed hereinabove. The expandable polystyrene particles were NOVA Chemicals R330B. These particles were first pre-expanded in a Hirsch batch pre-expander to a core bulk density of 2.5 pounds per cubic foot and then were aged for 24 hours before being injected in a mold. NOVA Chemicals R330B beads have a density of 40 pounds per cubic foot and about 4.0% pentane as a blowing agent.

Several grape boxes were molded from these aged pre-puff or pre-expanded particles using the KG 606 or Kurtz 812 molding machine. The dimensions of these grape boxes were 20×16×6.25 inches. These grape boxes had a wall thickness of 0.5 inch and 1.0 inch, and were molded to evaluate the methyl bromide sorption dependence on the foam volume of each box (the thinner the wall, the less foam volume in each box).

The molded EPS grape boxes were tested for methyl bromide sorption using the following method:

One grape box was placed inside the testing chamber, which was sealed with a flat cover by applying strip caulking around the lip of the chamber to ensure the chamber was gas-tight.

Methyl bromide gas was introduced into the chamber by a gas-tight syringe, with the aliquot taken from a TEDLAR bag filled with pure gas. The pure gas was obtained from a cylinder of standard fumigation grade methyl bromide.

The amount of gas injected into the chamber was determined by the USDA Treatment Manual, Interim Edition, published by Plant Protection Quarantine of APHIS (Animal and Plant Health Inspection Service, see Table 1). The recommendations in this manual are based on uses authorized under provisions of FIFRA (Federal Insecticide, Fungicide, and Rodenticide Act). The amount of gas injected was dependent on the commodity and the temperature of the commodity, which are listed in the treatment schedules in the Treatment Manual, as represented in Table 1.

An air conditioner controlled the external temperature to the specific level shown in Table 1. Here, a 45° F. temperature and the corresponding dosage were used. After the gas was injected, the gas in the chamber was sampled with a portable gas chromatograph that was calibrated with methyl bromide from concentrations of 1 to 20,000 ppmv (parts per million volume). Data were collected every 180 seconds over 4 hours. The minimum USDA (United States Daily Allowance) concentrations levels for phytotoxicity are based on the first two hours of exposure. The dynamic aeration period concentrations are important for worker and environmental exposure considerations.

TABLE 1

USDA Fumigation Protocol
Grapes from Chile/External Feeders/Insects other than Mediterranean Fruit Fly or Vine Moth

| Temperature | Dosage Rate lb/1000 ft³ | Minimum Concentration (oz/1000 ft³) | |
|---|---|---|---|
| | | 0.5 hr (80%) | 2 hrs (60%) |
| 80 F. or above | 1.5 | 19 | 14 |
| 70-79 F. | 2.0 | 26 | 19 |
| 60-69 F. | 2.5 | 32 | 24 |
| 50-59 F. | 3.0 | 38 | 29 |
| 40-49 F. | 4.0 | 48 | 38 |

Ref: USDA PPQ Treatment Schedules T101-i-2/T101-i-2-1

The methyl bromide sorption during the first 2 hours of the exposure period was calculated using the following equation:

MeBr sorption rate=$1-C_2/C_0$ where $C_2$ is the methyl bromide concentration at the end of the 2-hour methyl bromide exposure period, $C_0$ is the initial methyl bromide concentration of the exposure period.

The methyl bromide sorption rate was used in this Example to compare the sorption ability of different grape boxes at the specific test conditions (same test chamber, same number of grape box tested, and same dosage of methyl bromide used, etc.).

The test results show that the methyl bromide sorption rate of the EPS grape box having a wall thickness of 1.0 inch was 51.8% while the grape box having a wall thickness of 0.5 inch was 25.9%. As indicated in this Example, the reduction of the box foam volume by reducing the box wall thickness substantially decreases the methyl bromide sorption of the EPS grape boxes.

Example 2

For Example 2, Example 1 was repeated except that the raw R330B EPS beads from NOVA Chemicals were substituted with NOVA Chemicals 34RB particles, which have a density of 40.0 pounds per cubic foot and approximately 5.9% pentane as a blowing agent.

The test results show that the methyl bromide sorption rate of the EPS grape box having a wall thickness of 1.00 inch was 38% while the grape box having a wall thickness of 0.5 inch was 30%. These results show that a reduction of the box foam volume by reducing the box wall thickness substantially decreases the methyl bromide sorption of the EPS grape boxes.

Example 3

For Example 3, Example 1 was repeated except that the foam volume of each EPS grape box was reduced by eliminating the top wall of the grape box, i.e. open-top EPS grape box instead of decreasing the wall thickness of the grape boxes as was done in Examples 1 and 2.

The test results show that the methyl bromide sorption rate of standard EPS grape boxes (1.0 inch wall thickness and with top wall) was 64% while the grape box with 1.0 inch wall thickness without a top wall (open-top box) was 45.4%. The reduction of the box foam volume by reducing the box wall thickness and by removing a top wall substantially decreases the methyl bromide sorption of EPS grape boxes.

While the present invention has been particularly set forth in terms of specific embodiments thereof, it will be evident to those skilled in the art that numerous variations and details of the invention may be made without departing from the instant invention as defined in the appended claims.

What is claimed is:

1. A method for improving the resistance of fumigant sorption in a produce container in a fumigation process, the steps comprising:
   making a produce container by
   pre-expanding expandable polymer particles comprising expandable polymer particles having a density ranging from about 40.0 pounds per cubic foot to about 32.0 pounds per cubic foot to form pre-expanded particles with a core bulk density ranging from about 12.5 pounds per cubic foot to 2.0 pounds per cubic foot and an outer skin with a density ranging from about 40.0 to about 32.0 pounds per cubic foot and a thickness ranging from about 0.10 to about 2.0 microns; and
   forming said produce container from said pre-expanded particles by injecting the pre-expanded particles into a mold having the shape of a produce container and heating the closed mold to further expand and fuse the pre-expanded particles to form said produce container;
   wherein the residual fumigant level of the produce container is not more than 5 ppm based on the weight of the produce container after the produce container has been introduced to a fumigant in a sealed chamber such that the concentration of the fumigant in the chamber is at least 48 ounces/1000 ft$^3$ for an initial 30 minutes and at least 38 ounces/1000 ft$^3$ for a subsequent 90 minutes and aeration air is subsequently exchanged for the fumigant in the chamber.

2. A method of claim 1, wherein said produce container has a wall thickness ranging from about 0.25 inch to about 2.0 inches.

3. A method of claim 1, wherein said pre-expanded polymer particles have a particle size of greater than 300 microns.

4. A method of claim 3 wherein said polymer particles are comprised of polystyrene particles.

5. A method of improving the resistance of fumigant sorption in a produce container made from expandable polymer particles in a fumigation process, the steps comprising:
   making a produce container by producing expandable polymer particles having a density ranging from about 40.0 to about 32.0 pounds per cubic foot;
   pre-expanding said expandable particles to form pre-expanding particles having a low density core and a high density skin, said low density core ranging from about 12.5 to about 2.0 pounds per cubic foot and said high density skin ranging from about 40.0 to about 32.0 pounds per cubic foot;
   using said pre-expanded particles to produce a produce container by injecting the pre-expanded particles into a mold having the shape of the produce container and heating the closed mold to further expand and fuse the pre-expanded particles to form said produce container;
   wherein the residual fumigant level of the produce container is not more than 5 ppm based on the weight of the produce container after the produce container has been introduced to a fumigant in a sealed chamber such that the concentration of the fumigant in the chamber is at least 48 ounces/1000 ft$^3$ for an initial 30 minutes and at least 38 ounces/1000 ft$^3$ for a subsequent 90 minutes and aeration air is subsequently exchanged for the fumigant in the chamber.

6. A method of claim 5 wherein said polymer particles are polystyrene particles.

7. The method according to claim 1, wherein the fumigant comprises methyl bromide.

8. The method according to claim 5, wherein the fumigant comprises methyl bromide.

* * * * *